(12) United States Patent
Amano

(10) Patent No.: US 9,833,208 B2
(45) Date of Patent: Dec. 5, 2017

(54) BODY SECTION IMAGING APPARATUS

(75) Inventor: Masaharu Amano, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 477 days.

(21) Appl. No.: 13/634,354

(22) PCT Filed: Mar. 12, 2010

(86) PCT No.: PCT/JP2010/001788
§ 371 (c)(1),
(2), (4) Date: Sep. 12, 2012

(87) PCT Pub. No.: WO2011/111119
PCT Pub. Date: Sep. 15, 2011

(65) Prior Publication Data
US 2012/0324648 A1 Dec. 27, 2012

(51) Int. Cl.
*A61B 6/00* (2006.01)
*A61B 6/03* (2006.01)
*A61B 6/04* (2006.01)

(52) U.S. Cl.
CPC .......... *A61B 6/4447* (2013.01); *A61B 6/037* (2013.01); *A61B 6/04* (2013.01); *A61B 6/0407* (2013.01); *A61B 6/0457* (2013.01); *A61B 6/0478* (2013.01); *A61B 6/4482* (2013.01); *A61B 6/501* (2013.01); *A61G 2210/50* (2013.01)

(58) Field of Classification Search
CPC ....... A61B 6/04; A61B 6/4447; A61B 6/0478; A61G 7/018; A61G 7/002; A61G 13/02; A61G 13/06; A61G 2210/50; A61G 6/0457; A61G 6/0407; A61G 6/501; A61G 6/4482; A61G 6/037

USPC ........ 5/600, 601, 607, 611; 378/17, 20, 208, 378/209
See application file for complete search history.

(56) References Cited

U.S. PATENT DOCUMENTS

| | | | | |
|---|---|---|---|---|
| 3,206,188 A | * | 9/1965 | Douglass, Jr. | 5/614 |
| 3,868,103 A | * | 2/1975 | Pageot et al. | 5/614 |
| 4,195,829 A | * | 4/1980 | Reser | 5/614 |

(Continued)

FOREIGN PATENT DOCUMENTS

| JP | 01-308532 A | 12/1989 |
|---|---|---|
| JP | 02-209132 A | 8/1990 |

(Continued)

OTHER PUBLICATIONS

Chinese Office Action issued in Chinese Application No. 201080065400.0 dated Apr. 1, 2014.

*Primary Examiner* — David E Sosnowski
*Assistant Examiner* — David R Hare
(74) *Attorney, Agent, or Firm* — McDermott Will & Emery LLP

(57) ABSTRACT

There are provided a gantry with an opening having a central axis inclined so that the opening is directed obliquely downward, a chair disposed obliquely below the gantry, and having an inclined surface for supporting a patient M so that the central axis of the opening and a body axis A of the patient M become parallel, and a chair moving mechanism for driving at least one of the gantry and the chair to insert the patient M into the opening parallel to the central axis of the opening of the gantry. Thus, images can be picked up of the patient M in a comfortable position safely and efficiently.

22 Claims, 12 Drawing Sheets

(56) References Cited

U.S. PATENT DOCUMENTS

| | | | |
|---|---|---|---|
| 4,422,177 A * | 12/1983 | Mastronardi et al. | 378/17 |
| 4,961,208 A * | 10/1990 | Okada | 378/18 |
| 4,989,142 A * | 1/1991 | Crawford | 382/131 |
| 5,014,688 A * | 5/1991 | Fast | 606/242 |
| 5,273,043 A * | 12/1993 | Ruike | 600/436 |
| 5,574,763 A * | 11/1996 | Dehner | 378/17 |
| 6,400,791 B1 * | 6/2002 | Schwarz | 378/17 |
| 6,831,961 B1 * | 12/2004 | Tybinkowski et al. | 378/4 |
| 6,978,499 B2 * | 12/2005 | Gallant et al. | 5/600 |
| 7,224,764 B2 * | 5/2007 | Sukovic et al. | 378/19 |
| 7,742,562 B2 * | 6/2010 | Weber | 378/68 |
| 8,190,234 B2 * | 5/2012 | Green et al. | 600/415 |

FOREIGN PATENT DOCUMENTS

| | | |
|---|---|---|
| JP | 06-014913 A | 1/1994 |
| JP | 10-314160 A | 12/1998 |
| JP | 2005-176955 A | 7/2005 |
| JP | 2006-212229 A | 8/2006 |
| JP | 2009-236726 A | 10/2009 |
| WO | 03103496 A1 | 12/2003 |

* cited by examiner

BODY SECTION IMAGING APPARATUS

RELATED APPLICATIONS

This application is the U.S. National Phase under 35 U.S.C. §371 of International Application No. PCT/JP2010/001788, filed on Mar. 12, 2010.

TECHNICAL FIELD

This invention relates to a body section imaging apparatus for picking up sectional images of a patient inserted in an opening of a gantry.

BACKGROUND ART

As shown in FIG. 19, a conventional body section imaging apparatus 201 includes a gantry 203 having a cylindrical opening 202 for inserting a patient M, the opening 202 having a central axis 202a extending horizontally, a bed device 205 having a top board 204 for supporting the patient M in a supine position, and a top board moving mechanism 207 for moving the top board 204 vertically and horizontally. The body section imaging apparatus 201 having such construction may be a PET (Positron Emission Tomography) apparatus, for example.

The PET apparatus includes a multilayer detector ring 213 having detector rings in multiple layers with radiation detectors arranged in a ring form around the opening 202 of the gantry 203. Data is collected by carrying out coincidence counting with the multilayer detector ring 213 of two radial rays (e.g. gamma rays) released in 180° opposite directions from a patient medicated with a radioactive drug. A sectional image is acquired from image reconstruction of the collected data (see Patent Document 1, for example).

In such body section imaging apparatus 201, an operation for placing the patient M on the bed device 205, inserting, for example, the head of the patient M into the opening 202 of the gantry 203, and making positional adjustment to an imaging position is generally carried out as follows. That is, first, as shown in FIG. 19, the top board 204 of the bed device 205 is lowered vertically, and the patient M is seated on the top board 204 having been lowered to a low position. Then, as shown in FIG. 20, the patient M seated on the top board 204 is made to take a supine position. As shown in FIG. 21, the top board 204 with the patient M placed in the supine position thereon is raised vertically to an imaging height position. As shown in FIG. 22, the top board 204 raised to the imaging height position with the patient M placed thereon is moved horizontally to insert the head of the patient M into the opening 202 of the gantry 203, and positional adjustment is made to an effective field of view of the multilayer detector ring.

As this type of apparatus, apparatus have been disclosed which include a gantry body and a bed device capable of picking up images of a supine position and a seated position (see Patent Documents 2 and 3, for example).

In the apparatus disclosed in Patent Document 2, the gantry body is rotatably supported through support rods projecting from upper opposite ends thereof by a support frame. And, the gantry body is constructed to be rotatable and fixable to a predetermined inclination angle by a drive device using the support rods as fulcrum. On the other hand, the bed device has a reclining mechanism to be capable of setting a patient to a supine position or a seated position. The bed device has a lift device for vertically movably supporting a bed body, and a horizontally moving device which can move back and forth along guide rails. That is, the bed body is constructed movable vertically and horizontally.

In the apparatus disclosed in Patent Document 3, the gantry body is rotatably supported by a lift member through a tilt rod (support rod). The tilt rod has a sector connecting gear fixed thereto. The connecting gear is constructed to receive power from a drive mechanism through a gear mechanism which moves a lift member vertically. That is, the gantry body is movable up and down with the lift member, and the gantry body is constructed tiltable by the connecting gear rotating with ascent of the lift member. An examination table (bed device) is constructed movable vertically and horizontally.

[Patent Document 1]
Unexamined Patent Publication No. 2009-236726
[Patent Document 2]
Unexamined Patent Publication H6-14913
[Patent Document 3]
Unexamined Patent Publication H10-314160

DISCLOSURE OF THE INVENTION

Problem to be Solved by the Invention

However, the conventional apparatus have the following drawbacks. When images are picked up of a patient lying supine on the top board as in the prior art, it is necessary to lower the top board to a position low enough for the patient to get seated. Moreover, the patient must lie on the thin and narrow top board, and the operator must take great care about safety to avoid the patient falling from the top board. This is the same also when letting the patient off the top board after examination. It is desirable to carry out image pickup (examination) while the patient stays in a comfortable position. An operation for inserting the patient into the opening of the gantry requires a biaxial movement in which the top board is raised vertically and then moved horizontally for transport into the opening of the gantry. It will be difficult to make positional adjustment, and the operation will consume time accordingly.

This invention has been made having regard to the state of the art noted above, and its object is to provide a body section imaging apparatus which can pick up images of a patient in a safe and comfortable position, and that efficiently.

Means for Solving the Problem

To fulfill the above object, this invention provides the following construction. A body section imaging apparatus of this invention comprises a gantry with an opening having a central axis inclined so that the opening is directed obliquely downward; a support table disposed obliquely below the gantry, and having an inclined surface for supporting a patient so that the central axis of the opening and a body axis of the patient become parallel; an imaging position moving mechanism for driving the support table to insert the patient into the opening parallel to the central axis of the opening; a gantry moving mechanism for driving the gantry to move the gantry parallel to the central axis of the opening; struts for integrally supporting the gantry, the support table, the imaging position moving mechanism, and the gantry moving mechanism; and an imaging angle change mechanism for changing an angle to a horizontal direction of the gantry, the support table, the imaging position moving mechanism, and the gantry moving mechanism in an integrated state.

According to the body section imaging apparatus of this invention, the gantry is arranged to have the central axis of the opening inclined so that the opening is directed obliquely downward. The support table for supporting the patient is disposed obliquely below the gantry, and the surface of the support table for supporting the patient is inclined, so that the central axis of the opening of the gantry and the body axis of the patient placed on the support table will become parallel. Further, the imaging position moving mechanism drives the support table to insert the patient into the opening parallel to the central axis of the opening. That is, the central axis of the opening of the gantry, the body axis of the patient placed on the support table, and the direction of movement of the imaging position moving mechanism are arranged in parallel, and are inclined. Consequently, an operation to insert the patient into the opening of the gantry, that is, movement from a position where the patient mounts and dismounts to an imaging position can be made directly in a uniaxial direction. Therefore, positional adjustment can be made easily. Since positional adjustment can be made easily, positional adjustment can be made in a short time. Therefore, image pickup can be carried out efficiently. Since only movement in a uniaxial direction is required, there are few elements subject to misalignment in positional adjustment, which provides excellent reproducibility and facilitates securing of positional accuracy.

Where the support table is moved, it is not necessary as in the conventional apparatus to bend the waist in visually making positional adjustment, and therefore the operator can carry out the positional adjustment in an easy posture. Since the surface for supporting the patient is inclined, and since one end of the support table is close to the floor because of the inclination of the supporting surface, the patient can be placed more safely than with the conventional apparatus. Consequently, the operator's burden is lightened. Since the surface for supporting the patient is inclined, images can be picked up of the patient in a comfortable position. Since the gantry and the support table are inclined, their installation area can be made small.

Where the gantry are moved by the gantry moving mechanism, before moving the support table supporting the patient, the gantry may be moved to a position suitable to the operator, whereby positional adjustment can be made in an easy posture for the operator.

The operator can select a position such as a seated position or supine position suitable for examination by changing the angle of the integrated gantry, support table, imaging position moving mechanism, and gantry moving mechanism with the imaging angle change mechanism. Since an angle of the support table can be selected, images can be picked up of the patient in a comfortable position. The angle of each of the gantry, support table, imaging position moving mechanism, and gantry moving mechanism is not changed individually, but the angle thereof is changed in the integrated state. Therefore, the central axis of the opening of the gantry, the direction of the body axis of the patient placed on the support table, and the moving direction of the imaging position moving mechanism can be maintained parallel. Therefore, imaging can be carried out efficiently, with positional adjustment being easy and being made in a short time. Maintenance can be carried out easily by changing the angle and moving the gantry down to a low position.

In the body section imaging apparatus of this invention, one example of the support table is a chair for seating the patient. By using a chair as the support table, the patient can assume a seated position. Since a backrest of the chair is inclined, images can be picked up of the patient in a comfortable position. The patient can mount and dismount with increased safety. Consequently, the patient can mount and dismount safely alone without assistance of the operator, thereby to lighten the burden on the operator. Further, one example of the support table is a top board for supporting the patient. By using a top board as the support table, images can be picked up of the patient in a stretched position.

It is preferred that the body section imaging apparatus of this invention comprises a chair angle change mechanism for changing an angle between a backrest and a seat of the chair; wherein the chair angle change mechanism carries out an operation for inclining backward and an operation for raising forward the backrest relative to the seat which is fixed. The chair angle change mechanism carries out an operation for raising the backrest of the chair when allowing the patient to mount and dismount. The backrest is reclined to a predetermined angle when picking up images of the patient. Consequently, the patient, who is an old person, for example, may feel uneasy in sitting on the chair if the backrest of the chair is angled, but such uneasiness can be eliminated. That is, the patient can mount and dismount safely, and images can be picked up of the patient in a comfortable position.

It is preferred that the body section imaging apparatus of this invention comprises a chair angle change mechanism for changing an angle between a backrest and a seat of the chair; wherein the chair angle change mechanism carries out an operation for inclining forward and an operation for raising backward the seat relative to the backrest which is fixed, to change the angle between the backrest and the seat according to an angle of the imaging angle change mechanism. When the integrated gantry and so on are raised forward with the imaging angle change mechanism, the chair angle change mechanism carries out an operation for raising the seat backward relative to the backrest which is fixed. When the integrated gantry and so on are inclined backward with the imaging angle change mechanism, the chair angle change mechanism carries out an operation for inclining the seat forward relative to the backrest which is fixed. The above can prevent the position of the patient becoming unstable, with the legs of the patient being raised, for example. The patient may feel uneasy in sitting on the chair if the backrest of the chair is angled, but such uneasiness can be eliminated. That is, the patient can mount and dismount safely, and images can be picked up of the patient in a comfortable position.

It is preferred that the body section imaging apparatus of this invention comprises a footrest angle change mechanism for changing an angle between a top board body and a footrest for supporting the patient's feet of the top board; wherein the footrest angle change mechanism carries out an operation for inclining forward and an operation for raising backward the footrest relative to the top board body which is fixed. When allowing the patient to mount and dismount from the top board, the footrest angle change mechanism carries out an operation for inclining the footrest forward relative to the top board body which is fixed, to change the angle so that a surface for supporting the patient's feet of the footrest will become horizontal, for example. When picking up images of the patient, an operation is carried out for raising the footrest backward relative to the top board body which is fixed, to change the angle so that the supporting surface of the top board and the surface for supporting the patient's feet of the footrest will become perpendicular to each other, for example. Consequently, the patient can mount and dismount with increased safety.

It is preferred that the body section imaging apparatus of this invention comprises a thickness direction moving mechanism for moving the support table in a direction of thickness of the patient placed on the support table. Thus, even when the body thickness of each patient is different, the central axis of the opening of the gantry and the body axis of the patient can substantially be brought into agreement. Therefore, since the patient does not need to be moved close to an inner wall of the opening of the gantry, positional adjustment is easy and can be carried out in a short time. That is, images can be picked up of the patient in a comfortable position, and user-friendliness is provided for the operator.

It is preferred that, in the body section imaging apparatus of this invention, the gantry is designed for the head. This allows the opening of the gantry to have a reduced diameter, which allows for a reduced number of radiation detectors arranged around the opening of the gantry, thereby to hold down manufacturing cost. The installation area may be made small also.

Effects of the Invention

With the body section imaging apparatus according to this invention, the central axis of the opening of the gantry, the body axis of the patient placed on the support table, and the direction of movement of the imaging position moving mechanism are arranged in parallel, and are inclined. Consequently, an operation to insert the patient into the opening of the gantry, that is, movement from a position where the patient mounts and dismounts to an imaging position can be made directly in a uniaxial direction. Therefore, positional adjustment can be made easily. Since positional adjustment can be made easily, positional adjustment can be made in a short time. Therefore, image pickup can be carried out efficiently. Since the surface for supporting the patient is inclined, images can be picked up of the patient in a comfortable position, and the patient can mount and dismount safely. Where the gantry are moved by the gantry moving mechanism, before moving the support table supporting the patient, the gantry may be moved to a position suitable to the operator, whereby positional adjustment can be made in an easy posture for the operator. The operator can select a position such as a seated position or supine position suitable for examination by changing the angle of the integrated gantry, support table, imaging position moving mechanism, and gantry moving mechanism with the imaging angle change mechanism. Since an angle of the support table can be selected, images can be picked up of the patient in a comfortable position. The angle of each of the gantry, support table, imaging position moving mechanism, and gantry moving mechanism is not changed individually, but the angle thereof is changed in the integrated state. Therefore, the central axis of the opening of the gantry, the direction of the body axis of the patient placed on the support table, and the moving direction of the imaging position moving mechanism can be maintained parallel. Therefore, imaging can be carried out efficiently, with positional adjustment being easy and being made in a short time. Maintenance can be carried out easily by changing the angle and moving the gantry down to a low position.

Figure 1:
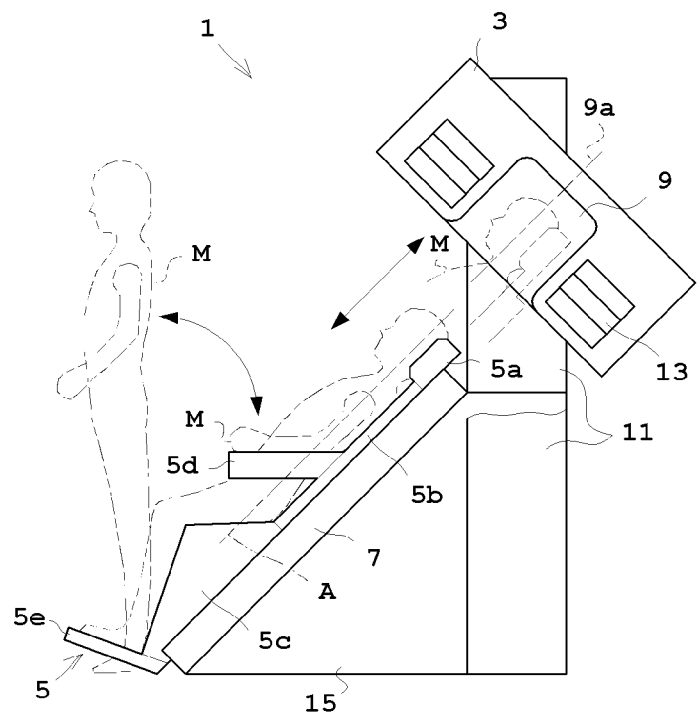
FIG. 1 is a side view showing an outline construction, partly in section, of a PET apparatus for the head according to Embodiment 1.

DESCRIPTION OF REFERENCES 1, 1A-1E . . . PET apparatus for the head
3 . . . gantry
5 . . . chair
5b . . . backrest
5c . . . seat
7 . . . chair moving mechanism
9 . . . opening
9a . . . central axis
11 . . . struts
37 . . . control unit
41 . . . gantry moving mechanism
57 . . . chair angle change mechanism
69 . . . struts
71 . . . imaging angle change mechanism
97 . . . thickness direction moving mechanism 111 . . . top board
111b . . . top board body
111c . . . footrest
113 . . . top board moving mechanism
115 . . . footrest angle change mechanism Embodiment 1

Figure 2:
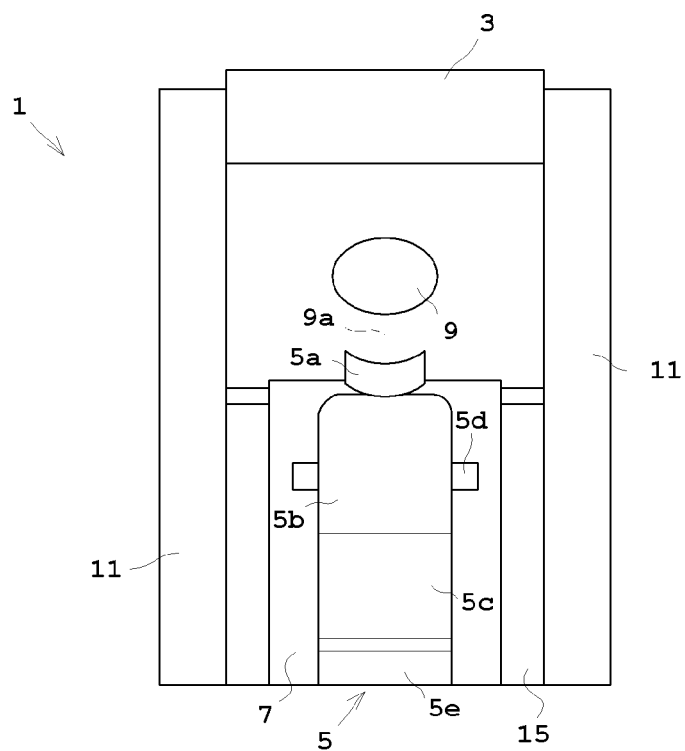
FIG. 2 is a front view showing the outline construction of the PET apparatus for the head according to Embodiment 1.
Figure 3:
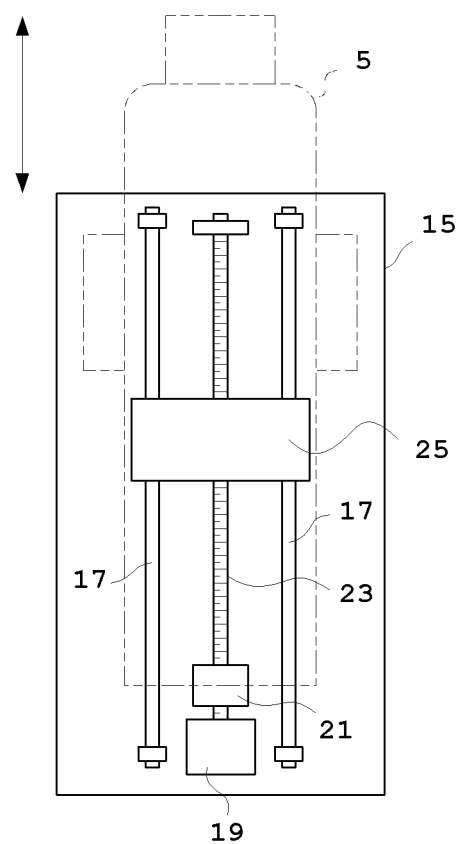
FIG. 3 is a view showing a construction of a chair moving mechanism.
Figure 4:
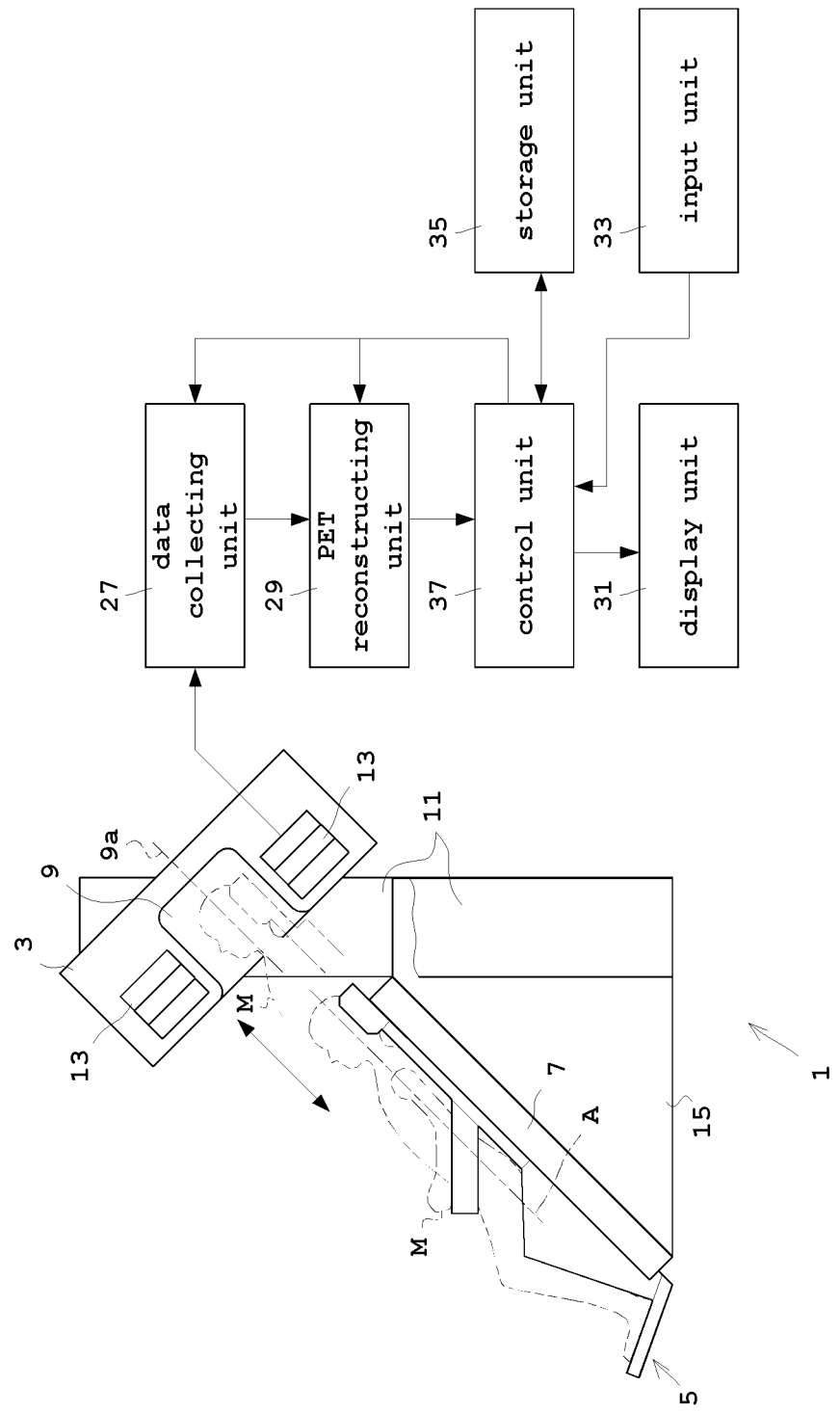
FIG. 4 is a block diagram showing a control system of the PET apparatus for the head.

Embodiment 1 of this invention will be described hereinafter with reference to the drawings. A PET apparatus for the head will be described as an example of the body section imaging apparatus of this invention. FIG. 1 is a side view showing an outline construction, partly in section, of a PET apparatus for the head according to Embodiment 1, and FIG. 2 is a front view thereof. FIG. 3 is a view showing a construction of a chair moving mechanism, and FIG. 4 is a block diagram showing a control system of the PET apparatus for the head.

Reference is made to FIGS. 1 and 2. A PET apparatus for the head 1 in this embodiment includes a gantry 3, a chair 5 for seating a patient M, and a chair moving mechanism 7 for moving this chair 5 to an imaging position. The PET apparatus for the head 1 corresponds to the body section imaging apparatus in this invention. The chair moving mechanism 7 corresponds to the imaging position moving mechanism in this invention.

The gantry 3 is supported at opposite side surfaces thereof by a pair of struts 11, and is disposed obliquely upward of the chair 5. The gantry 3 has an opening 9 of approximately cylindrical or polygonal tube shape for receiving the head of the patient M. This opening 9 has an inclined (e.g. by 45 degrees) central axis 9a. That is, the entire gantry 3 is disposed as inclined toward the chair 5 on which the patient M is seated.

The opening 9 of the gantry 3 is surrounded by a multilayer detector ring 13 constructed of multiple layers in the axial direction of ring detectors with a plurality radiation detectors arranged in a ring form. That is, a plurality of radiation detectors are provided for reliably enclosing the head of the patient M at the time of image pickup.

Each radiation detector has a scintillator block, a light guide, and a photomultiplier tube (none being shown), for example. The scintillator block is formed of a plurality of scintillators. The scintillator block converts, into light, gamma rays generating from the patient medicated with a radioactive drug. The light guide guides the converted light, and the photomultiplier tube carries out photoelectric conversion and outputs electric signals.

The chair 5 has a headrest 5a, a backrest 5b, a seat 5c, armrests 5d, and a footrest 5e. The chair 5 has a mechanism which can adjust the position of headrest 5a while maintaining it parallel to the central axis 9a of the opening 9 of the gantry 3 according to the sitting height of the patient M. The chair 5 is supported by a support block 15 through the chair moving mechanism 7, and the support block 15 is supported by the pair of struts 11. That is, the chair 5 is supported by the struts 11 through the chair moving mechanism 7 and support block 15. The chair 5 is disposed obliquely below the gantry 3. The chair 5 is arranged to have inclined surfaces of the headrest 5a and backrest 5b for contacting the patient M, so that the central axis 9a of the opening 9 of the gantry 3 and body axis A of the upper body of the seated patient M become parallel.

The chair moving mechanism 7 drives the chair 5 parallel to the central axis 9a of the opening 9 of the gantry 3 in operations to insert the head of the patient M into the opening 9 of the gantry 3 and draw it out therefrom. That is, the chair moving mechanism 7 is constructed to cause movement in an oblique direction only in a uniaxial direction from a mounting and dismounting position where the patient M mounts and dismounts from the chair 5 to the imaging position where the head of the patient M is placed in the opening 9. As shown in FIG. 3, the chair moving mechanism 7 has guide rails 17, a motor 19, a speed reducer 21, a screw shaft 23, and a connector 25.

Specifically, a pair of guide rails 17 are mounted on the support block 15 to extend parallel to the central axis 9a of the opening 9 of the gantry 3. On this pair of guide rails 17, the connector 25 connected to the chair 5 is supported to be movable along the guide rails 17 (direction of arrow). The support block 15 has, arranged thereon, the motor 19, speed reducer 21 and screw shaft 23, which are constructed such that rotation of the motor 19 is transmitted to the screw shaft 23 through the speed reducer 21. The screw shaft 23 is constructed to penetrate the connector 25 and a penetrated portion is meshed with the screw thread of the screw shaft 23. That is, when the motor 19 makes forward or reverse rotation to rotate the screw shaft 23 through the speed reducer 21, a driving force acts on the connector 25. Therefore, the connector 25 moves along the pair of guide rails 17.

Reference is made to FIG. 4. The PET apparatus for the head 1 includes a data collecting unit 27 for collecting emission data detected by the multilayer detector ring 13, and a PET reconstructing unit 29 for reconstructing the emission data collected by this data collector 27. Further, the PET apparatus for the head 1 includes a display unit 31 having a monitor or the like for displaying sectional images or the like resulting from image reconstruction, an input unit 33 having a mouse, a keyboard and so on for the operator to set inputs, a storage unit 35 for storing sectional images and others, and a control unit 37 having a CPU and the like for performing overall control to operate the various components such as the chair moving mechanism 7 appropriately by executing various programs.

Next, operation of the PET apparatus for the head 1 will be described. First, the patient M medicated with a radioactive drug is seated on the chair 5 of the PET apparatus 1. The chair moving mechanism 7 is operated to move the chair 5 with the seated patient M in a body axis direction of the patient M, i.e. parallel to the central axis 9a of the opening 9 of the gantry 3. The movement is made to the position where the head of the patient M is placed in the opening 9 of the gantry 3, i.e. a position in the effective field of view of the multilayer detector ring 13. In the state of the head of the patient M placed in the opening 9 of the gantry 3, gamma rays released from the head of the patient M are detected.

Annihilation gamma-ray pairs released from a localized site of the radioactive drug with which the patient M was medicated beforehand are detected by the multilayer detector ring 13 provided around the opening 9. The data collecting unit 27 checks positions of the scintillator blocks of the radiation detectors where the gamma rays are detected in the multilayer detector ring 13, and incidence timing thereof, and determines, to be proper data, the emission data sent in only when the gamma rays are incident at the same time on two scintillator blocks which are in mutually opposite positions across the patient M. When a gamma ray is incident only on one of the scintillator blocks, the data collecting unit 27 treats it not as a gamma ray produced by annihilation of a positron but as a noise, and determines the emission data sent in at this time to be noise, and carries out a process to reject it, for example. In this way, it is known that the radioactive drug is localized on a straight line linking the two positions in the multilayer detector ring 13 where the gamma rays are detected at the same time.

Subsequently, the emission data collected by the data collecting unit 27 is sent into the PET reconstructing unit 29 as projection data. The PET reconstructing unit 29 reconstructs the projection data to obtain a sectional image showing a distribution of the radioactive drug in the head of the patient M. The sectional image obtained is outputted to the display unit 31, for example. When the imaging is completed, the chair moving mechanism 7 moves the chair 5 to draw the head of the patient M out of the opening 9 of the gantry 3. A series of operations is ended by getting the patient M off the chair 5 in the mounting and dismounting position.

According to the PET apparatus for the head 1 having such construction, the gantry 3 is first arranged to have the central axis 9a of the opening 9 inclined so that the opening 9 is directed obliquely downward. The chair 5 for seating the patient M is disposed obliquely below the gantry 3, and the surfaces for contacting the patient M of the headrest 5a and backrest 5b of the chair 5 for seating the patient M are inclined, so that the central axis 9a of the opening 9 of the gantry 3 and the body axis 9a of the upper body of the patient M seated on the chair 5 will become parallel. Further, the chair moving mechanism 7 moves the chair 5 parallel to the central axis 9a of the opening 9 of the gantry 3 to insert the patient M into the opening 9 of the gantry 3. That is, the central axis 9a of the opening 9 of the gantry 3, the body axis A of the patient M seated on the chair 5, and the direction of movement of the chair moving mechanism 7 are arranged in parallel, and are inclined. Consequently, an operation to insert or withdraw the head of the patient M into/from the opening 9 of the gantry 3, that is, movement between the position where the patient M mounts and dismounts and the imaging position can be made directly in a uniaxial direction. Therefore, positional adjustment can be made easily. Since positional adjustment can be made easily, positional adjustment can be made in a short time. Therefore, image pickup can be carried out efficiently. Since only movements in a uniaxial direction are required, there are few elements subject to misalignment in positional adjustment, which provides excellent reproducibility and facilitates securing of positional accuracy. Since only movements in a uniaxial direction are required, the construction can be simplified which can hold down manufacturing cost.

Figure 5:
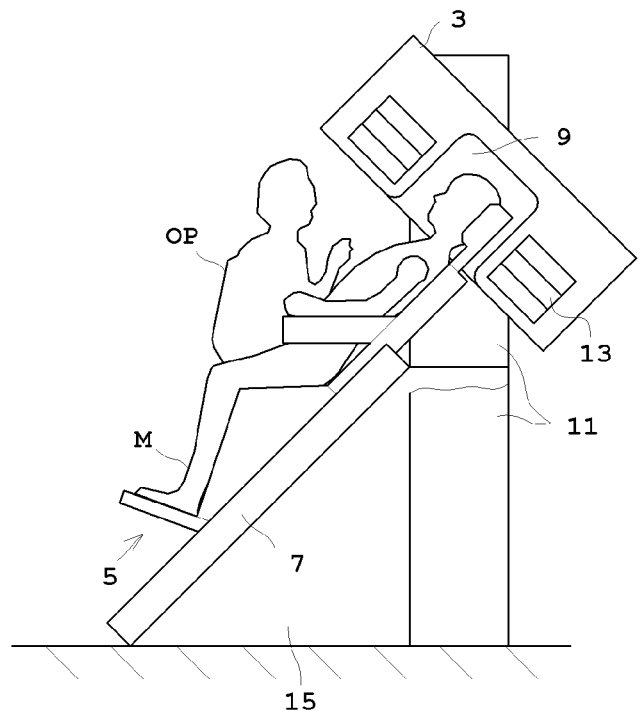
FIG. 5 is a view illustrating an effect of the PET apparatus for the head according to Embodiment 1.
Figure 22:
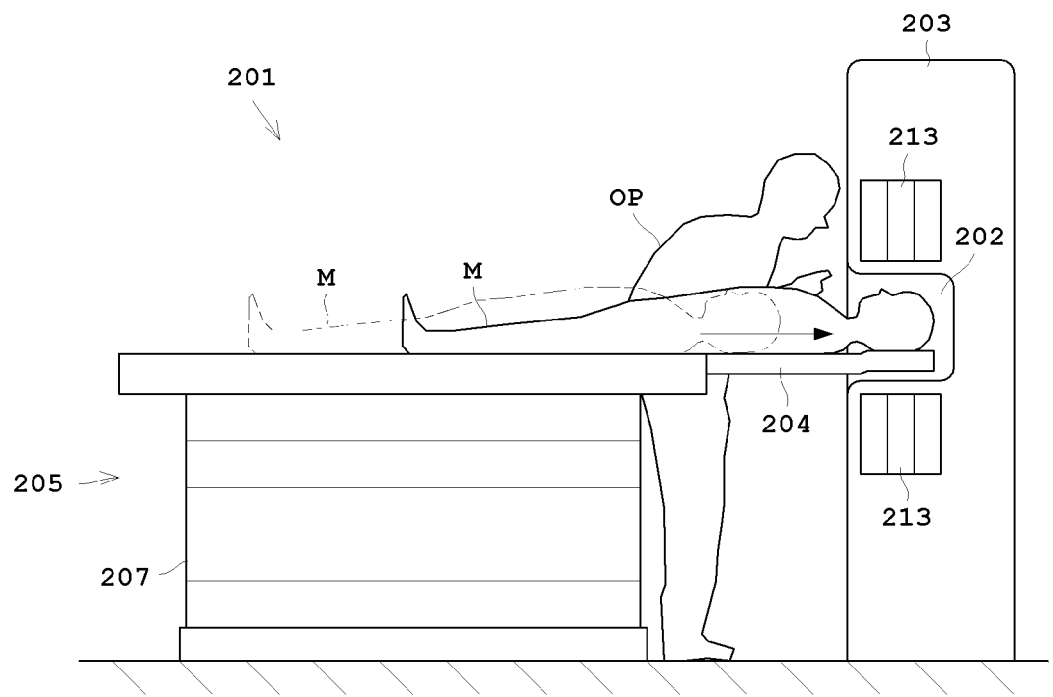
FIG. 22 is a view illustrating the outline construction and operation of the conventional PET apparatus for the head.

In the conventional apparatus, as shown in FIG. 22, the operator OP made positional adjustment visually while bending forward. On the other hand, as shown in FIG. 5, the gantry 3 and so on are inclined, and controls can be performed at a proper height for the operator, and thus the operator OP can make positional adjustment in an easy posture.

Since the conventional apparatus was arranged such that the top board had a horizontal supporting surface, the patient M had to lie supine on the top board. In this embodiment, on the other hand, the surface for supporting the patient M is inclined. Since one end thereof is close to the floor, the supporting surface is inclined, and moreover since the chair 5 is employed, the patient M can mount and dismount easily and safely. Consequently, the patient M can mount and dismount safely alone without assistance of the operator OP. That is, the burden on the operator OP can be lightened. Since the backrest 5b of the chair 5 is inclined, the patient can lean against the backrest 5b, and the position of the patient can be maintained. Therefore, images can be picked up of the patient M in a comfortable position. Since the gantry 3 and so on are inclined, their installation area can be made small.

Figure 6:
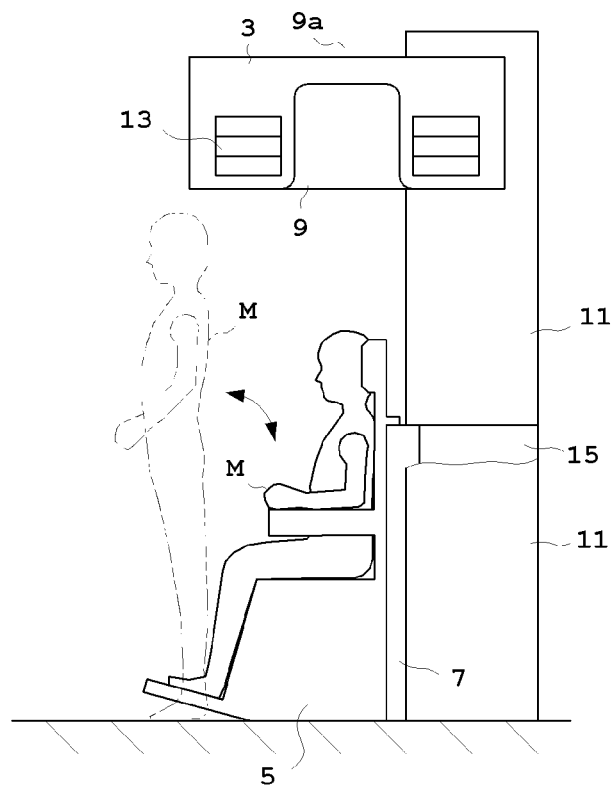
FIG. 6 is a view illustrating an effect of the PET apparatus for the head according to Embodiment 1.
Figure 7:
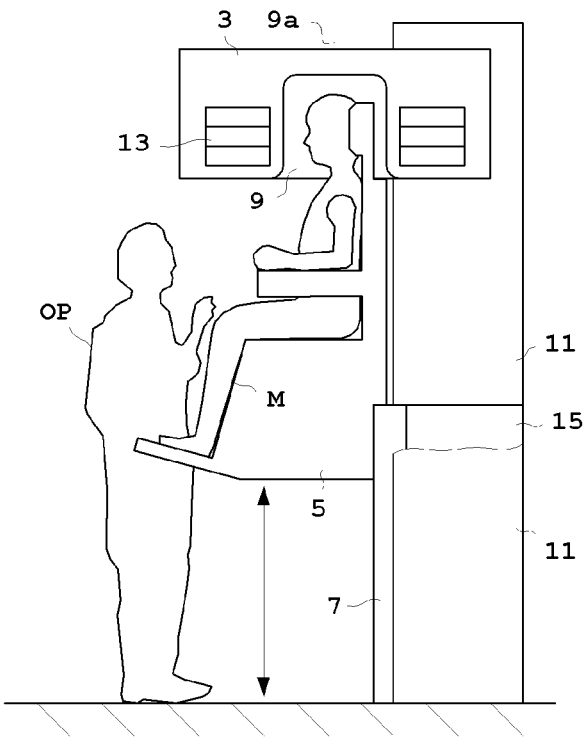
FIG. 7 is a view illustrating an effect of the PET apparatus for the head according to Embodiment 1.

Assume that, as shown in FIG. 6, the gantry 3 is arranged to have the central axis 9a of the opening 9 of the gantry 3 extending vertically, then the above-mentioned effect can be expected. However, the gantry 3 will have to be in a high position since enough space must be provided between the gantry 3 and chair 5 to allow the patient M to mount and dismount from the chair 5 without contacting the gantry 3. This brings about the following drawbacks. That is, as shown in FIG. 7, when the chair 5 with the seated patient is moved vertically to make positional adjustment, since there is a long distance between the position where the patient M mounts and dismounts and the imaging position, the vertical movement will take time. Further, with the gantry 3 located in the high position, the operator OP will have to look up when making positional adjustment, making the positional adjustment difficult. Since the imaging position is high, the patient M will feel uneasy. Since the gantry 3 is located in the high position, its maintenance is difficult.

Figure 8:
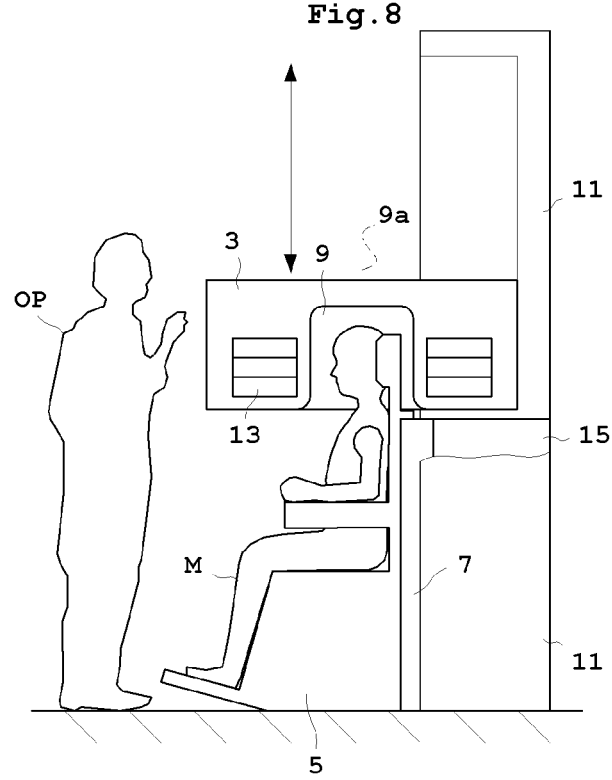
FIG. 8 is a view illustrating an effect of the PET apparatus for the head according to Embodiment 1.

It is conceivable to provide a mechanism for vertically moving the gantry 3, or a mechanism for vertically moving the gantry 3 and chair 5, as shown in FIG. 8. Where only the gantry 3 is movable up and down, the operator OP has to bend forward as noted hereinbefore, which makes positional adjustment difficult. Movement of the gantry 3 will give a feeling of oppression to the patient M. The gantry 3, which has a larger weight difference than the chair 5, will require time for vertical movement. Where the gantry 3 and chair 5 are movable up and down, the vertical movement of the gantry 3 will take time similarly. When the gantry 3 is not raised to a retreat position, there is a possibility of the patient M contacting the gantry 3.

Where the gantry 3 is arranged to have the central axis 9a of the opening 9 of the gantry 3 extending vertically, the surface for contacting the patient M of the backrest 5b of the chair 5 becomes vertical. Therefore, the patient M can intentionally hold the upper half of the body along the backrest 5b, but it is difficult to hold this position for a long time. That is, it is difficult to pick up images of the patient M in a comfortable position.

Embodiment 2

Figure 9:
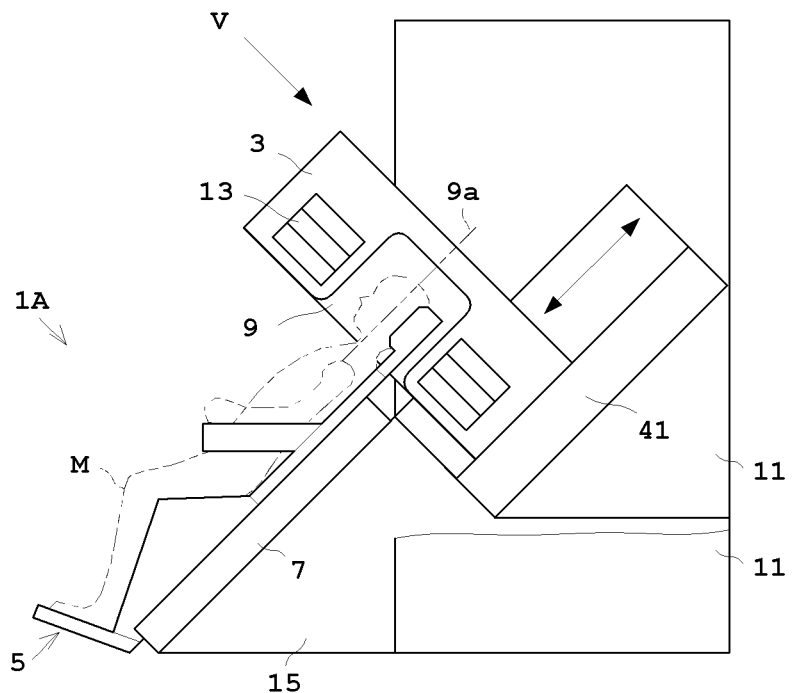
FIG. 9 is a side view showing an outline construction, partly in section, of a PET apparatus for the head according to Embodiment 2.
Figure 10:
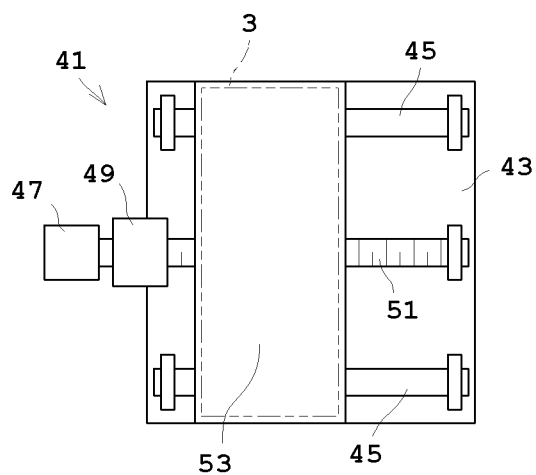
FIG. 10 is a view showing a construction of a gantry moving mechanism.

Next, Embodiment 2 of this invention will be described. FIG. 9 is a side view showing an outline construction, partly in section, of a PET apparatus for the head according to Embodiment 2. FIG. 10 is a view showing a construction of a gantry moving mechanism seen from sign V in FIG. 9. Components duplicating those in each foregoing embodiment will not be described.

Reference is made to FIG. 9. A PET apparatus for the head 1A in Embodiment 2 includes, further to the construction in Embodiment 1, a gantry moving mechanism 41 for driving the gantry 3 to insert a patient M into the opening 9 of the gantry 3 parallel to the central axis 9a of the opening 9. The gantry 3 is supported by the pair of struts 11 through the gantry moving mechanism 41. As shown in FIG. 10, the gantry moving mechanism 41 has a support deck 43 fixed to the pair of struts 11. Further, the gantry moving mechanism 41 has guide rails 45, a motor 47, a speed reducer 49, a screw shaft 51, and a gantry connector 53.

Specifically, a pair of guide rails 45 are arranged on the support deck 43 to be parallel to the central axis 9a of the opening 9 of the gantry 3. On this pair of guide rails 45, the gantry connector 53 connected to and supporting the gantry 3 is supported to be movable along the guide rails 45. The support deck 43 has, arranged thereon, the motor 47, speed reducer 49, and screw shaft 51, which are constructed such that output of the motor 47 is transmitted to the screw shaft 51 through the speed reducer 49. The screw shaft 51 is constructed to penetrate the gantry connector 53, and a penetrated portion is meshed with the screw thread of the screw shaft 51. That is, when the motor 47 makes forward or reverse rotation to rotate the screw shaft 51 through the speed reducer 49, a driving force acts on the gantry connector 53, whereby the gantry connector 53 moves along the pair of guide rails 45.

According to such PET apparatus for the head 1A in Embodiment 2, in addition to the effects of Embodiment 1, the operator OP, before moving the chair 5 seating the patient M with the chair moving mechanism 7 to make positional adjustment, can move the gantry 3 to a height position of the gantry 3 easy to carry out positional adjustment. Therefore, the operator OP can carry out positional adjustment in an easy posture.

In this embodiment, the PET apparatus for the head 1A has the chair moving mechanism 7 for moving the chair 5, and the gantry moving mechanism 41 for moving the gantry 3. However, the PET apparatus for the head may be constructed to have only the gantry moving mechanism 41 without having the chair moving mechanism 7. In this case, it will have disadvantages occurring when the operator OP makes positional adjustment visually in that the positional adjustment cannot be carried out in an easy posture, such as by having to bend forward, that moving the heavy gantry 3 will take a longer time than moving the chair 5, and that movement of the gantry 3 will give a feeling of oppression to the patient M. However, except for these points, the effects of Embodiment 1 are provided.

Embodiment 3

Figure 11:
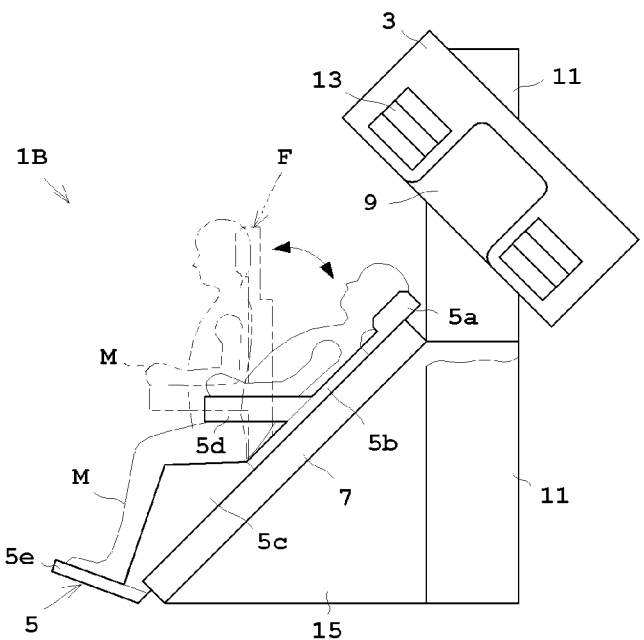
FIG. 11 is a side view showing an outline construction, partly in section, of a PET apparatus for the head according to Embodiment 3.
Figure 12:
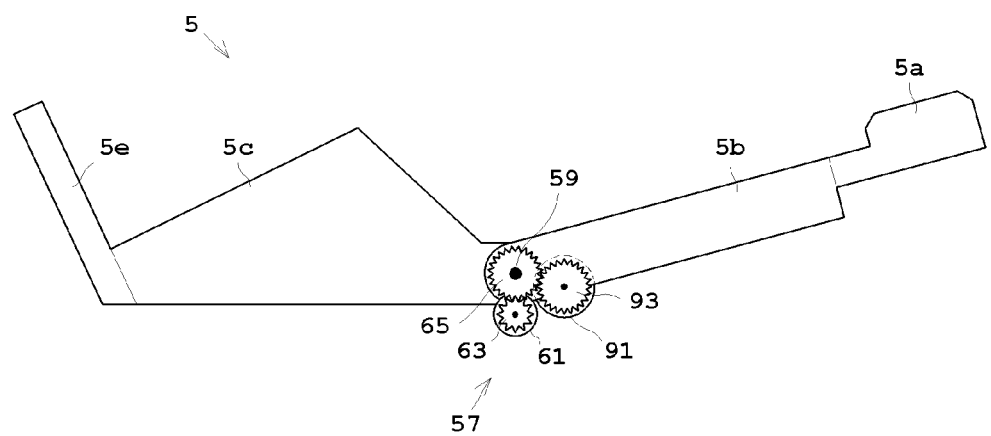
FIG. 12 is a view showing a construction of a chair angle change mechanism.

Next, Embodiment 3 of this invention will be described. FIG. 11 is a side view showing an outline construction, partly in section, of a PET apparatus for the head according to Embodiment 3. FIG. 12 is a view showing a construction of a chair angle change mechanism. Components duplicating those in each foregoing embodiment will not be described.

Reference is made to FIGS. 11 and 12. A PET apparatus for the head 1B includes, further to each foregoing embodiment, a chair angle change mechanism 57 for changing an angle between the backrest 5b and seat 5c of the chair 5. As shown in FIG. 12, the chair 5 has the backrest 5b and seat 5c connected together to be rotatable about a pivot shaft 59. Specifically, the pivot shaft 59 is fixed to the backrest 5b, and the seat 5c is connected to be rotatable about the pivot shaft 59. The seat 5c is supported by the support block 15 through the chair moving mechanism 7. The chair angle change mechanism 57 has a motor 61 fixed to the seat 5c, a gear 63 fixed to an output shaft of this motor 61, and a gear 65 meshed with this gear 63 and fixed to the pivot shaft 59. That is, when the chair angle change mechanism 57 operates, the motor 61 will make forward or reverse rotation, and the rotation will be transmitted from the gear 63 fixed to the output shaft of the motor 61, to the gear 65 fixed to the pivot shaft 59. At this time, the backrest 5b, pivot shaft 59 and gear 65 are in an integrated state. Consequently, an angle between the backrest 5b to which the pivot shaft 59 is fixed and the seat 5c can be increased or decreased. Therefore, the angle of the backrest 5b to the seat 5c supported by the support block 15 can be changed. That is, operations can be carried out to recline the backrest 5b, and to raise it forward.

When the patient M mounts and dismounts from the chair 5, as shown in two-dot chain lines with sign F in FIG. 11, the chair angle change mechanism 57 is operated to set the backrest 5b of the chair 5 to a forwardly raised position. At this time, the angle to the horizontal of the backrest 5b is set to a predetermined angle. And when picking up images of the patient M, the chair angle change mechanism 57 is operated to set the backrest 5b to a reclined position. It is constructed such that, when the backrest 5b is pushed down all the way, the body axis A of the upper half of the patient M seated on the chair 5 and the central axis 9a of the opening 9 of the gantry 3 become parallel.

According to such PET apparatus in Embodiment 3, the chair angle change mechanism 57 is operable to recline the chair backrest 5b backward of the chair 5, and to raise the backrest 5b forward. Consequently, when the patient M mounts and dismounts, the backrest 5b is in the position raised forward of the chair 5. The patient M, who is an old person, for example, may feel uneasy in sitting on the chair 5 with the backrest 5b reclining backward. Such uneasiness can be eliminated. That is, the patient M may be allowed to mount and dismount safely, and image pickup can be carried out while the patient M is kept in a comfortable position.

Embodiment 4

Figure 13:
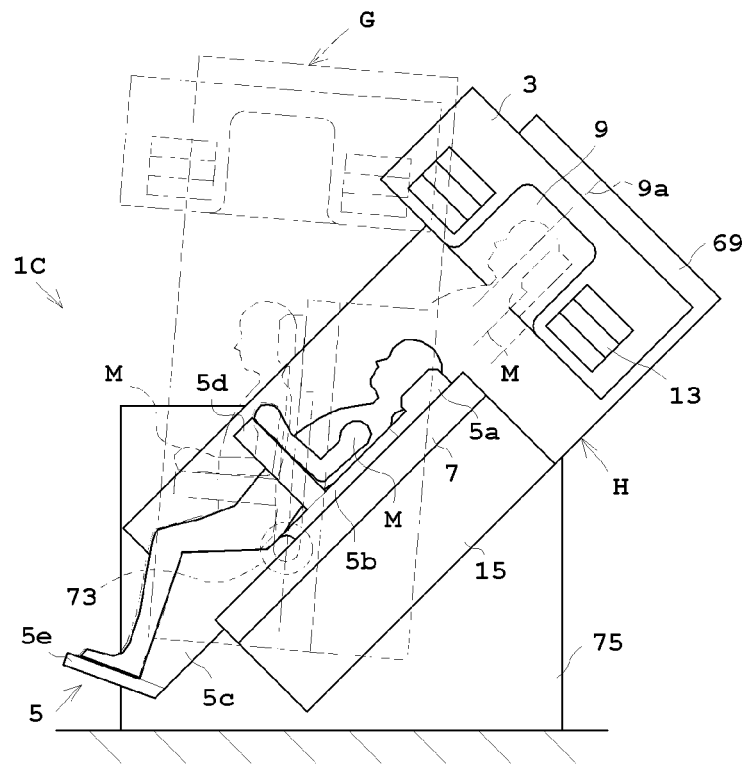
FIG. 13 is a side view showing an outline construction, partly in section, of a PET apparatus for the head according to Embodiment 4.
Figure 14:
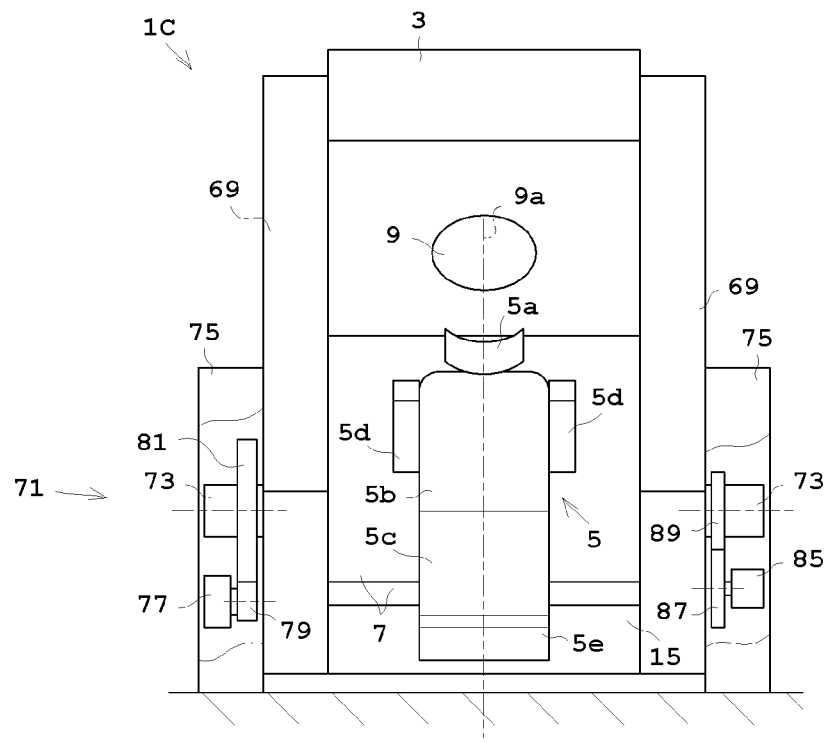
FIG. 14 is a front view showing, partly in section, the outline construction of the PET apparatus for the head according to Embodiment 4.
Figure 15:
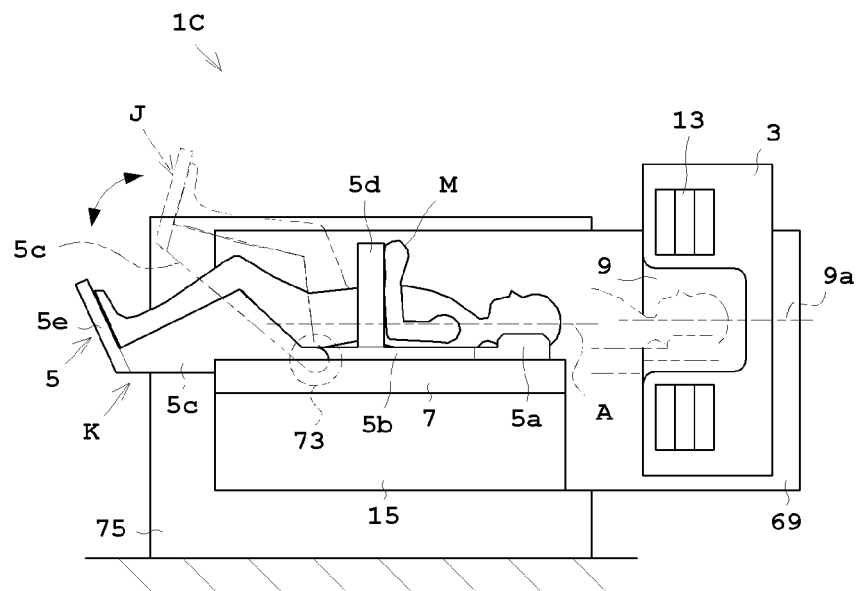
FIG. 15 is a view illustrating operation of an imaging angle change mechanism according to Embodiment 4.

Next, Embodiment 4 of this invention will be described. FIG. 13 is a side view showing an outline construction, partly in section, of a PET apparatus for the head according to Embodiment 4, and FIG. 14 is a front view thereof. FIG. 15 is a view illustrating operation of an imaging angle change mechanism. Components duplicating those in each foregoing embodiment will not be described.

Reference is made to FIGS. 13 and 14. A PET apparatus for the head 1C includes, further to each foregoing embodiment, struts 69 for integrally supporting the gantry 3 and chair 5, and an imaging angle change mechanism 71 for changing an angle of the integrated gantry 3 and chair 5 to the horizontal.

Specifically, the gantry 3 is supported by the struts 69, while the chair 5 is supported by the struts 69 through the chair moving mechanism 7 and support block 15. That is, the gantry 3, chair 5, chair moving mechanism 7, and support block 15 are integrated by the struts 69. Where, as shown in FIG. 9, the gantry moving mechanism 41 is provided for moving the gantry 3, the gantry 3 is supported by the struts 69 through the gantry moving mechanism 41. Where the chair moving mechanism 7 is not provided but only the gantry moving mechanism 41 is provided, the chair 5 is supported by the struts 69 through the support block 15.

Pivot shafts 73 are fixed laterally of the pair of struts 69, respectively. The pivot shafts 73 are rotatably supported by a base block 75. The integrated gantry 3 and so on have the angle changed about these pivot shafts 73. The imaging angle change mechanism 71 has a motor 77, a gear 79 fixed to an output shaft of this motor 77, and a gear 81 meshed with this gear 79 and fixed to the pivot shaft 73. That is, when the imaging angle change mechanism 71 operates, the motor 77 will make forward or reverse rotation, and the rotation will be transmitted from the gear 79 fixed to the output shaft of the motor 77, to the gear 81 fixed to the pivot shaft 73. Consequently, the integrated gantry 3 and so on will rotate about the pivot shafts 73 to have the angle of the central axis 9a of the opening 9 of the gantry 3 changed relative to the horizontal.

Reference is made to FIG. 15. When, for example, in a state of the backrest 5b and seat 5c of the chair 5 being fixed, the angle of the integrated gantry 3 and so on, i.e. the angle of the central axis 9a of the opening 9 of the gantry 3, is made small relative to the horizontal, as shown in two-dot chain lines with sign J in FIG. 15, the legs of the patient M will be raised to make an unstable position. When, in the state of the seat 5c shown in solid lines with sign K in FIG. 15, the angle of the integrated gantry 3 and so on is inclined to a large degree, the patient M will have difficulty in being seated to assume an unstable position.

So, the PET apparatus for the head 1C further includes the chair angle change mechanism 57 for changing the angle between the backrest 5b and seat 5c of the chair 5, as described in Embodiment 3. In this embodiment, as shown in FIG. 12, the chair 5 has the backrest 5b and seat 5c connected together to be rotatable about the pivot shaft 59. Specifically, the pivot shaft 59 is fixed to the backrest 5b, and the seat 5c is connected to be rotatable about the pivot shaft 59. The pivot shaft 59 is rotatably supported by the support block 15 through the chair moving mechanism 7. The chair angle change mechanism 57 has the motor 61 fixed to the seat 5c, the gear 63 fixed to then output shaft of this motor 61, and the gear 65 meshed with this gear 63 and fixed to the pivot shaft 59. That is, when the chair angle change mechanism 57 operates, the motor 61 will make forward or reverse rotation, and the rotation will be transmitted from the gear 63 fixed to the output shaft of the motor 61, to the gear 65 fixed to the pivot shaft 59. At this time, the backrest 5b, pivot shaft 59 and gear 65 are in an integrated state. Consequently, an angle between the backrest 5b to which the pivot shaft 59 is fixed and the seat 5c can be increased or decreased. Therefore, when the backrest 5b is fixed, it can change the angle of the seat 5c, and when the seat 5c is fixed, the angle of the backrest 5b can be changed. That is, when the backrest 5b is fixed, operations can be carried out to incline the seat 5c forward and raise it backward. When the seat 5c is fixed, operations can be carried out to recline the backrest 5b, and to raise it forward. Where only a construction for changing the angle of the seat 5c is provided, the backrest 5b may be supported by the support block 15 through the chair moving mechanism 7.

The chair angle change mechanism 57 is constructed to change the angle between the backrest 5b and seat 5c of the chair 5 according to an angle of the imaging angle change mechanism 71. Specifically, as shown in FIG. 14, the imaging angle change mechanism 71 includes an angle detector 85 in form of a rotary encoder for detecting an angle to the horizontal of the integrated gantry 3 and so on, a gear 87 fixed to an input shaft thereof, and a gear 89 meshed with this gear 87 and fixed to the pivot shaft 73. Similarly, as shown in FIG. 12, the chair angle change mechanism 57 includes an angle detector 91 in form of a rotary encoder for detecting the angle between the backrest 5b and seat 5c, and a gear 93 fixed to an input axis of this angle detector 91 and meshed with the gear 65.

Next, operation of the imaging angle change mechanism 71 and chair angle change mechanism 57 will be described, taking for example a case of changing the angle of the integrated gantry 3 and so on from the state shown in two-dot chain lines with sign G in FIG. 13, via the state shown in solid line with sign H in FIG. 13, to the state shown in solid lines with sign K in FIG. 15, or a case of changing the angle in the reversed direction.

When carrying out an operation to decrease the angle relative to the horizontal of the central axis 9a of the opening 9 of the gantry 3 of the integrated gantry 3 and so on, i.e. an operation to incline it backward of the patient M, the seat 5c of the chair 5 is inclined forward by the chair angle change mechanism 57 which changes the angle between the backrest 5b and seat 5c of the chair 5 according to and relative to an inclination of the integrated gantry 3 and so on. For example, when the imaging angle change mechanism 71 changes the angle by 5°, the chair angle change mechanism 57 changes the angle by −5°. Therefore, when seen from outside, the integrated gantry 3 and so on have their angle changed, except for the seat 5c and footrest 5e of the chair 5, and make a movement to incline backward of the patient M. When the inclination of the integrated gantry 3 and so on reaches a predetermined angle, the chair angle change mechanism 57 ends the operation for inclining the seat 5b forward. Therefore, when a further inclining is made backward, the seat 5c and footrest 5e of the chair 5 make a movement to incline backward with the integrated gantry 3 and so on.

On the other hand, when carrying out an operation to increase the angle to the horizontal of the integrated gantry 3 and so on, i.e. an operation to raise it forward of the patient M, the chair angle change mechanism 57 does not operate but the seat 5c and footrest 5e of the chair 5 move with the integrated gantry 3 and so on to the predetermined angle noted above. And when the above predetermined angle is reached, the chair angle change mechanism 57 carries out a backward raising operation which changes the angle between the backrest 5b and seat 5c of the chair 5 according to and relative to an inclination of the integrated gantry 3 and so on. Therefore, when seen from outside, the integrated gantry 3 and so on have their angle changed, except for the seat 5c and footrest 5e of the chair 5, and make a movement to rise forward of the patient M. The predetermined angle, preferably, is an angle at which the position of the patient M does not become unstable, e.g. an angle at which the body of the patient M does not bend.

In these operations, the control unit 37 monitors angle information from the angle detectors 85 and 91 provided for the imaging angle change mechanism 71 and chair angle change mechanism 57, respectively, and carries out proper controls.

Such PET apparatus for the head 1C in Embodiment 4, in addition to the effects of Embodiments 1 and 2, includes the struts 69 which integrally support the gantry 3, chair 5 and so on, and the imaging angle change mechanism 71 for changing the angle to the horizontal of the integrated gantry 3, chair 5 and so on. Therefore, the operator can select a position such as a seated position or supine position suitable for examination by changing the angle of the integrated gantry 3 and so on with the imaging angle change mechanism 71. The patient M can select an angle of the backrest 5b to be examined in a comfortable position. Maintenance can be carried out easily by changing the angle and moving the gantry 3 down to a low position.

The chair angle change mechanism 57 is provided for changing the angle between the backrest 5b and seat 5c of the chair 5. The chair angle change mechanism 57 carries out operations to incline forward, and to raise backward, the seat 5c relative to the fixed backrest 5b, thereby changing the angle between the backrest 5b and seat 5c according to the angle of the imaging angle change mechanism 71. Therefore, since the patient M assuming an unstable position is prevented by the angles, the patient M can undergo examination in a comfortable position. The patient M can mount and dismount from the chair 5 in the state where the angle to the horizontal of the integrated gantry 3, chair 5 and so on is increased to raise the integrated gantry 3, chair 5 and so on forward. Thus, the patient M can mount and dismount from the chair 5 simply and safely. Consequently, the operator need not give assistance. The patient M, who is an old person, for example, may feel uneasy in sitting if the backrest 5b of the chair 5 is angled. Such uneasiness can be eliminated.

Where the gantry 3, chair 5 and so on have their angles changed individually, each angle must be changed individually. On the other hand, since the gantry 3, chair 5 and so on are integrally supported by the struts 69, even when the angle of the imaging angle change mechanism 71 is changed, the central axis 9a of the opening 9 of the gantry 3, the body axis of the upper body of the patient M seated on the chair 5, and the direction of movement of the chair moving mechanism 7 remain in a parallel state. Therefore, the patient M can be positionally adjusted by moving in a uniaxial direction from the mounting and dismounting position to the imaging position.

Embodiment 5

Figure 16:
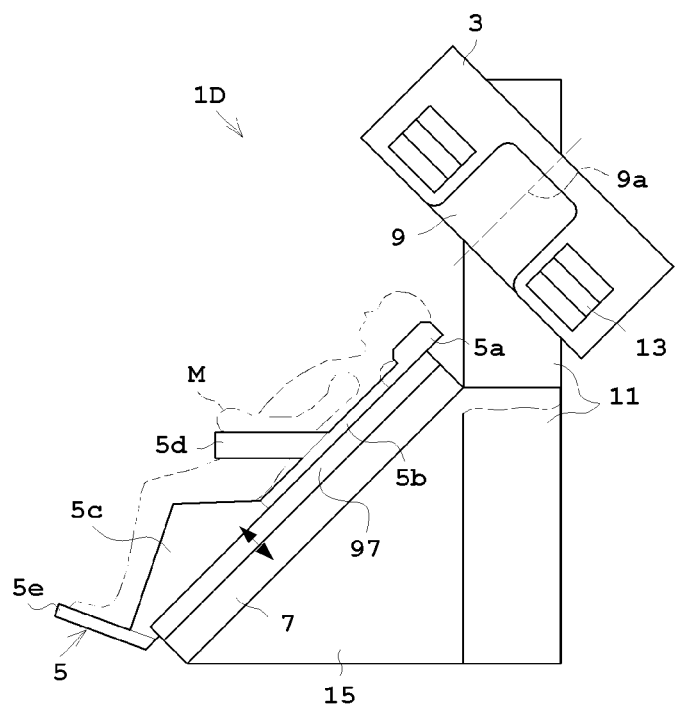
FIG. 16 is a side view showing an outline construction, partly in section, of a PET apparatus for the head according to Embodiment 5.
Figure 17:
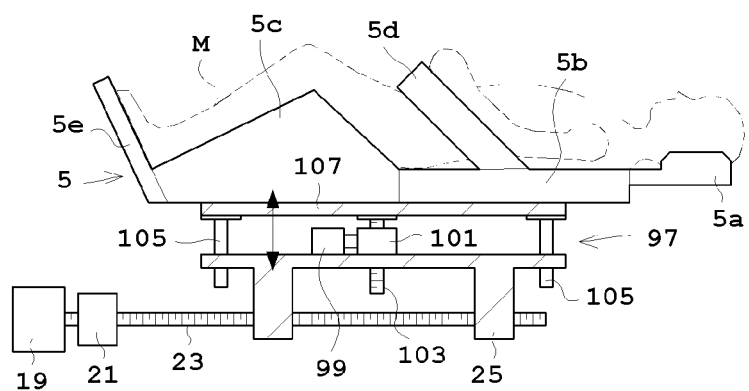
FIG. 17 is a view illustrating a construction of a thickness direction moving mechanism.

Next, Embodiment 5 of this invention will be described. FIG. 16 is a side view showing an outline construction, partly in section, of a PET apparatus for the head according to Embodiment 5. FIG. 17 is a view showing a construction of a thickness direction moving mechanism. Components duplicating those in each foregoing embodiment will not be described.

Reference is made to FIG. 16. A PET apparatus for the head 1D includes, further to each foregoing embodiment, a thickness direction moving mechanism 113 for moving the chair 5 in a direction of thickness of the patient M which is parallel to a direction perpendicular to the surface on which the patient M is placed, i.e. the surface for contacting the patient M of the backrest 5b of the chair 5. This thickness direction moving mechanism 97 is disposed between the chair 5 and the chair moving mechanism 7, for example.

As shown in FIG. 17, the thickness direction moving mechanism 97 has a motor 99, a speed reducer 101, a screw shaft 103, guide rails 105, and a chair support 107. The connector 25 of the chair moving mechanism 7 has, arranged thereon, the motor 99, speed reducer 101, and screw shaft 103 which are constructed such that output of the motor 99 is transmitted to the screw shaft 103 through the speed reducer 101. At this time, the screw shaft 103 is arranged to be parallel to the direction of thickness of the patient M. The screw shaft 103 has the rotation of the motor 99 transmitted thereto through the speed reducer 101, and the screw shaft 103 itself moves along the axis of the screw shaft 103. At one end of the screw shaft 103, the chair support 107 is arranged for supporting the chair 5. The guide rails 105 are fixed to the chair support 107 to extend along the direction of thickness of the patient M. The guide rails 105 penetrate the connecting member 25. Consequently, the chair support 107 is constructed movable along the guide rails 105 relative to the connecting member 25.

That is, when the motor 99 makes forward or reverse rotation, the screw shaft 103 itself moves in the direction of thickness of the patient M, whereby the chair support 107 moves along the guide rails 105. The moving distance of the thickness direction moving mechanism 97, preferably, is in such a range that the headrest 5a of the chair 5 does not jump out of the opening 9 of the gantry 3, for example, which, preferably, does not exceed 5 cm, for example.

Such PET apparatus for the head 1D in Embodiment 5, in addition to the effects of each foregoing embodiment, includes the thickness direction moving mechanism 97 for moving the chair 5 in the direction of thickness of the patient M. Thus, even when the body thickness of each patient M is different, the body axis of the patient M and the central axis 9a of the opening 9 of the gantry 3 can substantially be brought into agreement. Therefore, since the head of the patient M does not move close to an inner wall of the opening 9 of the gantry 3, positional adjustment is easy and can be carried out in a short time. Therefore, images can be picked up of the patient M in a comfortable position, and user-friendliness is provided for the operator.

Figure 19:
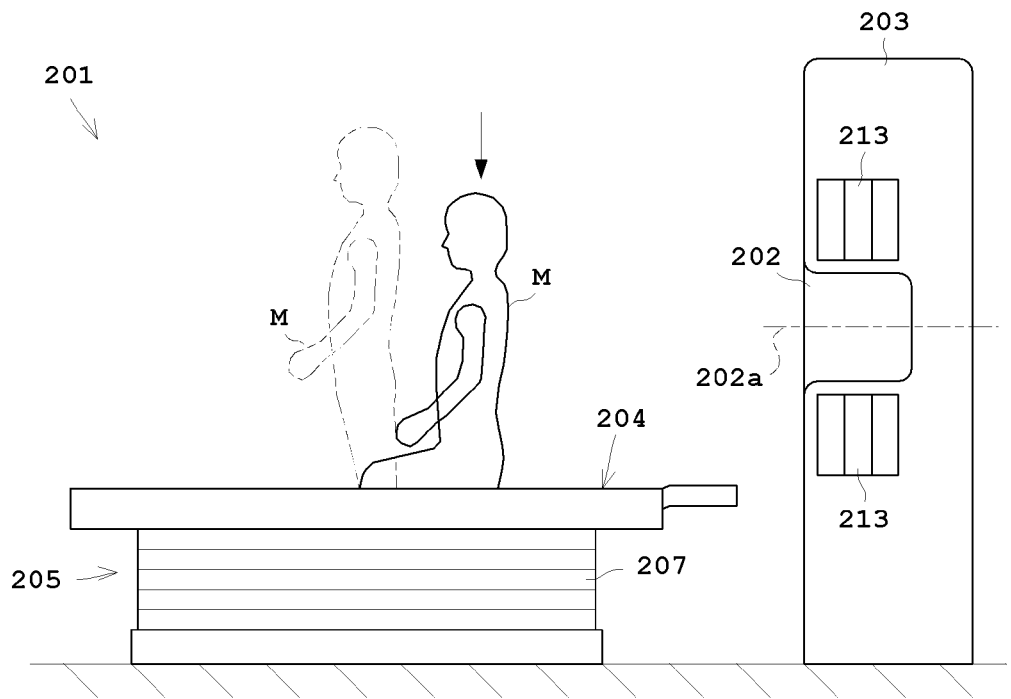
FIG. 19 is a view illustrating an outline construction and operation of a conventional PET apparatus for the head.
Figure 20:
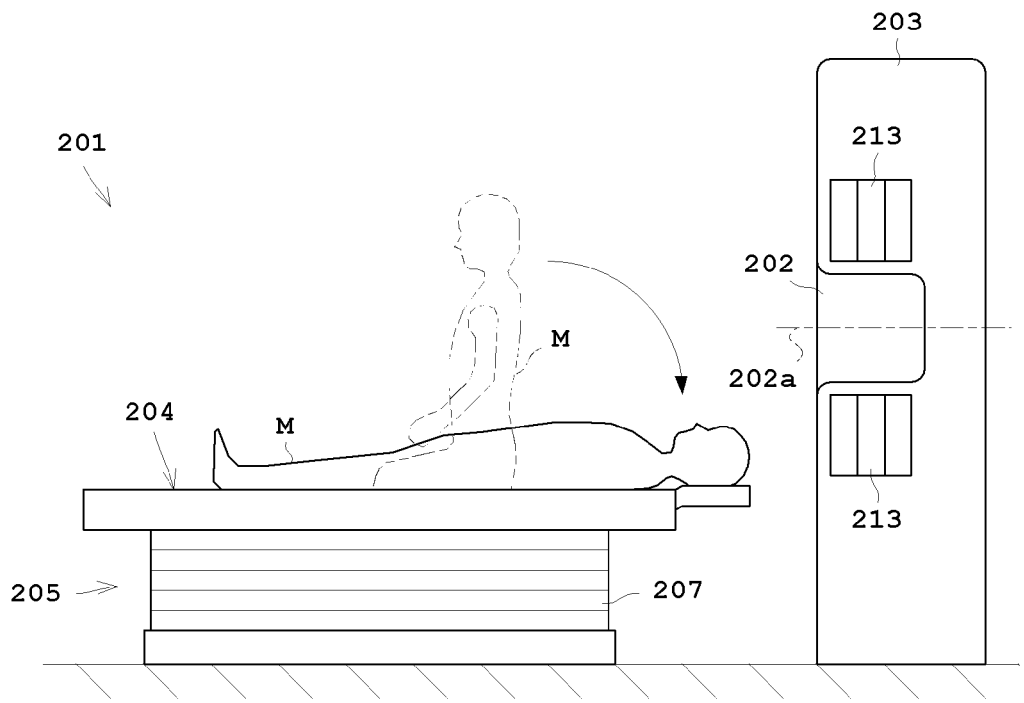
FIG. 20 is a view illustrating the outline construction and operation of the conventional PET apparatus for the head.
Figure 21:
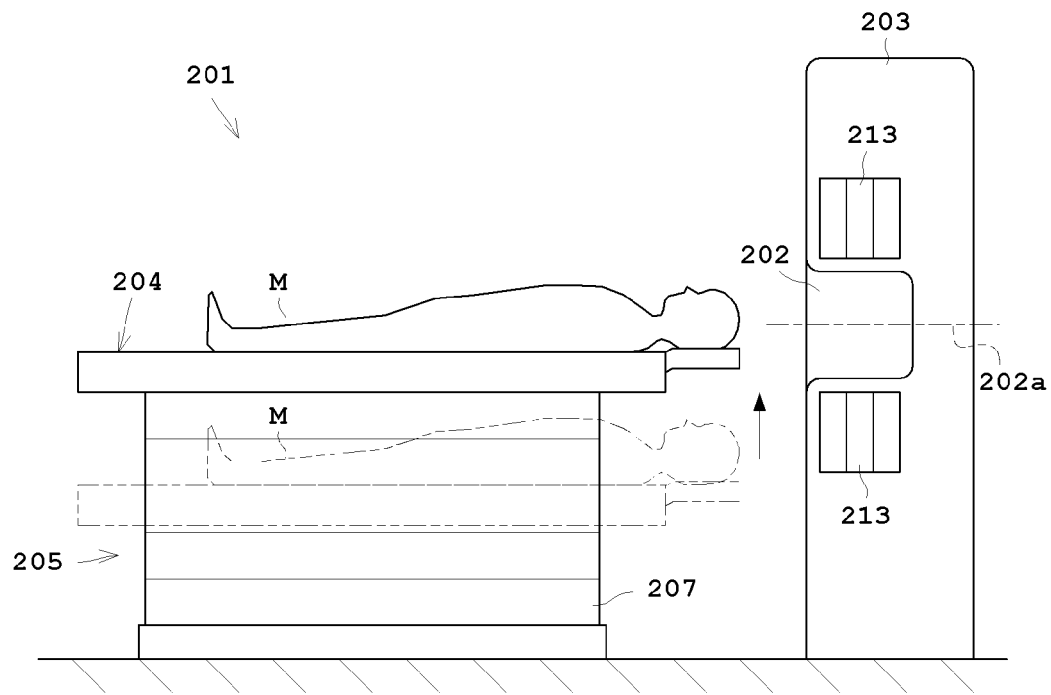
FIG. 21 is a view illustrating the outline construction and operation of the conventional PET apparatus for the head.

In this embodiment, positional adjustment of the patient M is made in biaxial directions as in the conventional apparatus as shown in FIG. 19. Basically, however, it is sufficient to make movement in a uniaxial direction between the position where the patient M mounts and dismounts from the chair 5 and the imaging position. This provides the effect that it is easy to make positional adjustment, and that in a short time as in foregoing Embodiment 1.

This embodiment provides the thickness direction moving mechanism 97 for moving the chair 5 in the direction of thickness of the patient, but this construction not limitative. That is, for example, a mechanism may be provided for varying the position of the headrest 5a in the direction of thickness, the headrest 5a or the backrest 5b may be changed to a sheet having a different thickness, or a spacer may be interposed between the patient M and the headrest 5a or backrest 5b.

Embodiment 6

Figure 18:
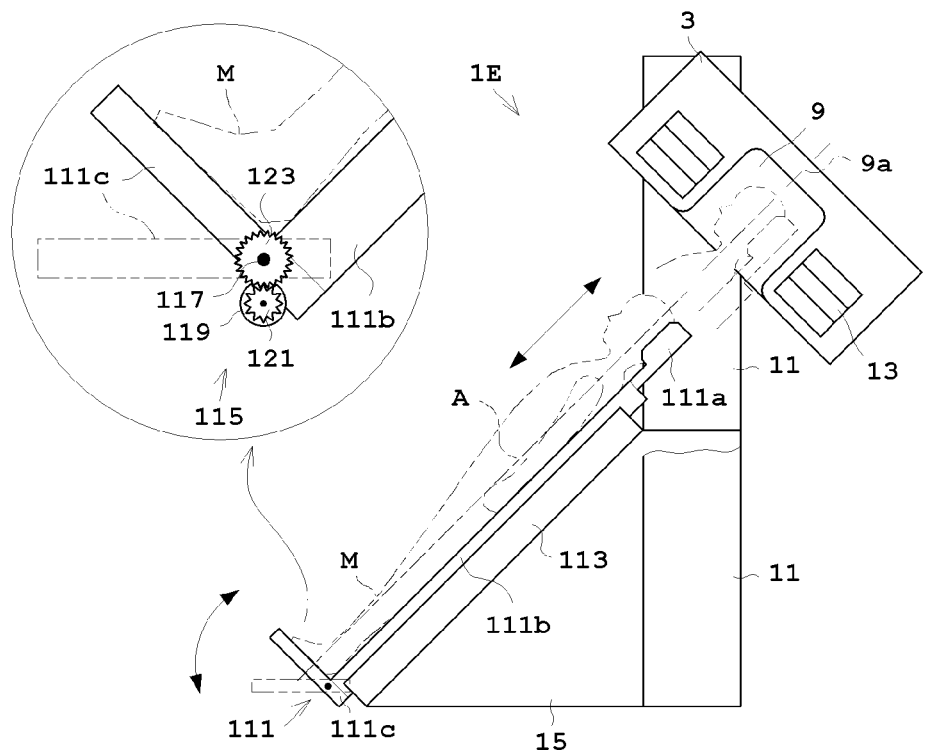
FIG. 18 is a side view showing an outline construction, partly in section, of a PET apparatus for the head according to Embodiment 6.

Next, Embodiment 6 of this invention will be described. FIG. 18 is a side view showing an outline construction, partly in section, of a PET apparatus for the head according to Embodiment 6. Components duplicating those in each foregoing embodiment will not be described.

Reference is made to FIG. 18. In each foregoing embodiment, the PET apparatuses for the head 1, 1A-1D has, as a support table for supporting the patient M, the chair 5 for seating the patient M, but this construction is not limitative. That is, a PET apparatus for the head 1E may have a top board 111 with a flat surface for supporting the patient M. In this case, the top board 111 includes a headrest 111a, a top board body 111b, and a footrest 111c. Further, the top board 111 includes a mechanism which can adjust the position of the headrest 111a while maintaining it parallel to the central axis 9a of the opening 9 of the gantry 3, according to the height of the patient M. The surface for supporting the patient M is inclined so that the body axis A of the patient M placed on the top board 111 become parallel to the central axis 9a of the opening 9 of the gantry 3 as in each foregoing embodiment. The PET apparatus for the head 1E has a top board moving mechanism 113 for moving the top board 97 parallel to the central axis 9a of the opening 9 of the gantry 3. The construction of the top board moving mechanism 113 is substantially the same as the construction of the chair moving mechanism 7, and so its description is omitted.

According to such PET apparatus for the head 1E in Embodiment 6, in addition to the effects of each foregoing embodiment, with the top board 111 as the support table for supporting the patient M, examination can be carried out of the patient M in a stretched position. The top board 111 is in an inclined arrangement. Therefore, since one end of the top board 111 is close to the floor, and the top board 111 is inclined, it is easier to place the patient M on the top board 111 than in the conventional apparatus, and mounting and dismounting can be made safely. Since the top board 111 is inclined, images can be picked up of the patient M in a comfortable position.

The PET apparatus for the head 1E may include a footrest angle change mechanism 115 for changing the angle between the top board body 111b and footrest 111c of the top board 111. The top board 111, as shown in an enlarged view in a round frame of FIG. 18, has a pivot shaft 117 fixed to the top board body 111b. The footrest 111c is connected to be rotatable about the pivot shaft 117. The top board body 111b is supported by the support block 15 through the top board moving mechanism 113. The footrest angle change mechanism 115 has a motor 119, a gear 121 fixed to an output shaft of this motor 119, and a gear 123 meshed with this gear 121 and fixed to the pivot shaft 117. That is, when the footrest angle change mechanism 115 operates, the motor 119 will make forward or reverse rotation, and the rotation will be transmitted from the gear 121 fixed to the output shaft of the motor 119, to the gear 123 fixed to the pivot shaft 117. Consequently, when the patient M mounts and dismounts, for example, a forward inclining operation is carried out to set the foot supporting surface in a substantially horizontal position. After the patient M is placed on the top board 111, a backward raising operation is carried out to set the foot supporting surface to a position substantially perpendicular to the surface of the top board body 111b on which the patient M is placed. Consequently, the patient M can mount and dismount from the top board 111 safely.

This invention is not limited to the foregoing embodiments, but may be modified as follows:

(1) In each foregoing embodiment, the opening 9 of the gantry 3 is surrounded by the multilayer detector ring 13 for detecting two radial rays released in 180° opposite directions from the radioactive drug given to the patient M beforehand, but this construction is not limitative. That is, an external radiation source which emits radiation (e.g. gamma ray) of the same type as the radioactive drug, i.e. radioisotope (RI), given to the patient M, and a ring detector for detecting the radiation from the external radiation source, may be further provided, to collect transmission data, and carry out absorption correction of emission data.

(2) In each foregoing embodiment, the opening 9 of the gantry 3 has a closed deep end as shown in FIG. 1, for example. This construction is not limitative. That is, the opening may have a construction to penetrate to the opposite side, i.e. what is called a tunnel form.

(3) Each foregoing embodiment is intended for the head which picks up images of the head of the patient M, but this construction is not limitative. That is, the opening 9 of the gantry 3 may be set large to pick up images of the neck, chest or other regions of the patient M.

(4) In each foregoing embodiment, the body section imaging apparatus is a PET apparatus which carries out coincidence counting of radiation released from a specific site of the patient M medicated with a radioactive drug, but this construction is not limitative. That is, the body section imaging apparatus may be an X-ray CT apparatus or MRI (magnetic resonance imaging) apparatus.

(5) In each foregoing embodiment, the mechanisms for changing position and angle are constructed of at least some of guide rails, motor, speed reducer, screw shaft, gears, and so on, but such constructions are not limitative. That is, for example, extending and contracting mechanisms such as hydraulic cylinders may be provided for moving the chair 5, top board 111 and gantry 3. Further, the angle between the backrest 5b and seat 5c, the angle of the integrated gantry 3 and so on, or the angle between the top board body 111b and footrest 111c may be changed.

The invention claimed is:

1. A body section imaging apparatus comprising:
a gantry with an opening having a central axis inclined so that the opening is directed obliquely downward;
a support table disposed obliquely below the gantry, and having an inclined surface for supporting a patient so that the central axis of the opening and a body axis of the patient become parallel with each other;
an imaging position moving mechanism configured to drive the support table to insert the patient into the opening, the imaging position moving mechanism moving the support table along the central axis of the opening;
a gantry moving mechanism configured to move the gantry along the central axis of the opening;
struts on which the gantry, the support table, the imaging position moving mechanism, and the gantry moving mechanism are mounted; and
a base configured to rotatably support the struts, and including an imaging angle change mechanism configured to drive the struts to change an angle of the struts relative to a horizontal surface, the gantry, the support table, the imaging position moving mechanism, and the gantry moving mechanism being moved together with the struts, wherein
the gantry is so mounted on the struts that an angle of the central axis of the opening changes together with the changing of the angle of the struts while maintaining a relative angle of the central axis and the struts constant.

2. The body section imaging apparatus according to claim 1, wherein the support table is a chair for seating the patient.

3. The body section imaging apparatus according to claim 1, wherein the support table is a top board for supporting the patient.

4. The body section imaging apparatus according to-claim 2, comprising:
a chair angle change mechanism for changing an angle between a backrest and a seat of the chair;
wherein the chair angle change mechanism carries out an operation for inclining backward and an operation for raising forward the backrest relative to the seat which is fixed.

5. The body section imaging apparatus according to claim 2, comprising a chair angle change mechanism for changing an angle between a backrest and a seat of the chair, wherein
the chair angle change mechanism carries out an operation for inclining forward and an operation for raising backward the seat relative to the backrest which is fixed, to change the angle between the backrest and the seat according to an angle of the imaging angle change mechanism.

6. The body section imaging apparatus according to claim 3, comprising a footrest angle change mechanism for changing an angle between a top board body and a footrest for supporting the patient's feet of the top board, wherein
the footrest angle change mechanism carries out an operation for inclining forward and an operation for raising backward the footrest relative to the top board body which is fixed.

7. The body section imaging apparatus according to claim 1, comprising a thickness direction moving mechanism for moving the support table in a direction of thickness of the patient placed on the support table.

8. The body section imaging apparatus according to claim 1, wherein the gantry is designed for the head.

9. The body section imaging apparatus according to claim 2, comprising a thickness direction moving mechanism for moving the chair in a direction of thickness of the patient placed on the chair.

10. The body section imaging apparatus according to claim 3, comprising a thickness direction moving mechanism for moving the top board in a direction of thickness of the patient placed on the top board.

11. The body section imaging apparatus according to claim 4, comprising a thickness direction moving mechanism for moving the chair in a direction of thickness of the patient placed on the chair.

12. The body section imaging apparatus according to claim 5, comprising a thickness direction moving mechanism for moving the chair in a direction of thickness of the patient placed on the chair.

13. The body section imaging apparatus according to claim 6, comprising a thickness direction moving mechanism for moving the top board in a direction of thickness of the patient placed on the top board.

14. The body section imaging apparatus according to claim 2, wherein the gantry is designed for the head.

15. The body section imaging apparatus according to claim 3, wherein the gantry is designed for the head.

16. The body section imaging apparatus according to claim 4, wherein the gantry is designed for the head.

17. The body section imaging apparatus according to claim 5, wherein the gantry is designed for the head.

18. The body section imaging apparatus according to claim 6, wherein the gantry is designed for the head.

19. The body section imaging apparatus according to claim 4, wherein the gantry is designed for the head.

20. The body section imaging apparatus according to claim 9, wherein the gantry is designed for the head.

21. The body section imaging apparatus according to claim 1, wherein the imaging position moving mechanism is configured to move the supporting table linearly along the central axis of the opening.

22. The body section imaging apparatus according to claim 1, wherein the gantry moving mechanism is configured to move the gantry linearly along the central axis of the opening.

* * * * *